United States Patent [19]

Poignant et al.

[11] 3,933,471

[45] Jan. 20, 1976

[54] COMPOSITIONS FOR CONTROLLING WEEDS

[75] Inventors: Pierre Poignant, Nyons; Bernard Thellot, Villefranche; Jacques Rognon, Ecully, all of France

[73] Assignee: PEPRO, Societe pour le Development et la Vente de Specialites, Lyon, France

[22] Filed: Feb. 1, 1974

[21] Appl. No.: 438,647

[30] Foreign Application Priority Data

Feb. 2, 1973 France .............................. 73.04389

[52] U.S. Cl. ................................. 71/120; 71/122
[51] Int. Cl.² ........................................ A01N 9/20
[58] Field of Search ............................. 71/120, 122

[56] References Cited
UNITED STATES PATENTS

2,655,447  10/1953  Todd ..................................... 71/120
3,649,241  3/1972  Fitzgerald et al. ..................... 71/120

OTHER PUBLICATIONS

Rogon et al., Chem. Abst. Vol. 79 (1973), 1260c.

Poignant, Chem. Abst. Vol. 73 (1970), 34082a.

French Pat. 1,475,686, Chem. Abst. Vol. 68, (1968), 2183q.

*Primary Examiner*—Lewis Gotts
*Assistant Examiner*—Catherine L. Mills
*Attorney, Agent, or Firm*—Browdy and Neimark

[57] ABSTRACT

Compositions for controlling weeds growing among cereal crops, cotton and soya containing a mixture of isopropylphenyl dimethylurea and dinitro tert.-butylphenol as active material.

12 Claims, No Drawings

COMPOSITIONS FOR CONTROLLING WEEDS

This invention relates to new herbicidal compositions for controlling weeds among crops.

More particularly, the invention relates to herbicidal compositions containing as active material a mixture of a urea corresponding to the formula:

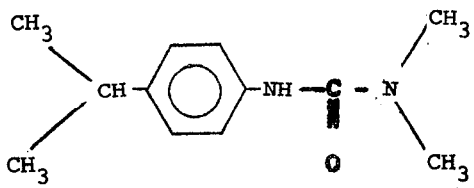

hereinafter referred to as I.P.U., and 2,4-dinitro-6-tert.-butylphenol, hereinafter referred to as dinoterbe.

Finally, the invention relates to the use of these compositions for controlling weeds among such crops as cereals, cotton, soya, both before and after emergence.

The use of I.P.U. for the selective control of weeds among cereal crops after emergence is described in particular in French Patent Application No. 2,125,240.

Although the use of this compound has considerable advantages over the previously known compounds, it has nevertheless been found that, when this compound is used in relatively high doeses, which can occasionally be of advantage under adverse treatment conditions, a certain level of phytotoxicity is apparent.

In addition, it would be desirable to be able to complete the action of I.P.U., which is primarily active against graminaceous weeds, by a herbicide that is more specifically active against dicotyledons.

It has been proposed to use dinoterbe for controlling dicotyledons among cereal crops.

It has now surprisingly been found that mixtures containing I.P.U. and dinoterbe or one of its derivatives show unexpected properties in relation to the properties which each of these compounds is known to have when used separately.

More particularly, it has been surprisingly found that the addition of certain quantities of dinoterbe or one of its derivatives to I.P.U. suppresses the phytotoxic phenomena observed in the case of I.P.U. alone, and that by contrast these mixtures show a degree of synergy with respect to economically significant wees which is reflected in an unexpectedly much higher destruction rate then that obtained with each of the products used on their own in the dame dose.

The observations made from the point of view of selectivity are all the more surprising insofar as in general, when one herbicidal compound is added to another herbicidal compound, the phytotoxicity phenomena attributable to one or other of these compounds tend to be aggravated by the presence of the other.

However, in the particular case of mixtures of I.P.U. and dinoterbe, the phenomenon observed is exactly the opposite to that which would be normally expected.

The above factors will be apparent from the following Examples which in addition illustrate an unexpected improvement in activity against certain important weeds.

EXAMPLE 1

The herbicidal properties and selective properties of the mixtures according to the invention were demonstrated by various tests under glass in comparison with the use of the separate constituents.

Thus, 10 × 15 cm pots are filled with clean soil, i.e. soil which has never been subjected to any herbicidal treatment. Seeds of various types of vegetables, the sensitivity of which are to be tested with respect to the herbicidal products, are placed on the soil. The seeds are then covered with a layer of soil in a thickness governed by the diameter of the seeds in accordance with conventional practice. When, after germination, the shoots have reached the stage of two true leaves, the herbicidal composition to be tested for post-emergence testing is sprayed onto the leaves. The herbicidal composition is in the form of a wettable powder prepared by mixing the following ingredients for one minute in a blade mill:

| | |
|---|---|
| active material to be tested | 20% |
| deflocculant (calcium lignosulphate) | 5% |
| wetting agent (sodium alkylaryl sulphonate) | 1% |
| filler (alumina silicate) | 74% |

This wettable powder is then mixed with a quantity of water calculated for spraying in the required dose per hectare.

In the case of pre-emergence treatment, the composition is sprayed after the seeds have been covered by the layer of earth.

In each test, one untreated control plant is set aside in order to be able to detect any inhibition in growth and in addition any absence of germination or defective growth of the plants attributable to the particular conditions.

The pots thus treated are then kept under glass for a certain period under constant conditions of humidity, temperature and lighting. After 5 weeks, the results are assessed, in particular by evaluating the percentage destruction of each of the species in relation to the control.

The various plants and weeds on which the tests were carried out are as follows:

| Species | Scientific Name | Symbol |
|---|---|---|
| Wild spring oat | Avena fatua | AV |
| Wheat | Triticum vulgare | BL |
| Barley | Hordeum distichum | OR |
| Rye-grass | Lolium italicum | RA' |
| Black grass | Alopecurus myosuroides | VU |
| White mustard | Sinapis alba | MO |
| May weed | Matricaria sp. | MT |
| Bind weed | Polygonum convolvulus | RE |

Under these conditions it was observed that, in doses of 2 kg/ha and 4 kg/ha, the mixture of equal parts of I.P.U. monomethylamine salt of dinoterbe is perfectly selective on wheat and barley, i.e. there is no phytotoxicity, while, in the same doses, I.P.U. is respectively lightly and heavily phytotoxic on these cereal crops.

EXAMPLE 2

The action of a 50/50 mixture of I.P.U. and of the monomethylamine salt of dinoterbe in a dose of 0.5 kg/ha is studied (as in Example 1) in comparison with that of each of the two constituents used individually in the same dose. The results, expressed as percentage destruction, are set out in the following Table:

| | | I-Pre-emergence test: | | | | | | | |
|---|---|---|---|---|---|---|---|---|---|
| | | Crops | | | | | Weeds | | |
| | BL | maize | cotton | soya | barnyard grass | RA | VU | MO | buck wheat |
| dinoterbeamine 0.5 kg/ha | 0 | 0 | 0 | 0 | 20 | 0 | 5 | 80 | 30 |
| I.P.U. 0.25 kg/ha | 0 | 0 | 0 | 0 | 30 | 50 | 40 | 10 | 50 |
| dinoterbe 0.5 + I.P.U. 0.25 | 0 | 0 | 0 | 0 | 65 | 70 | 65 | 99 | 85 |
| I.P.U. 0.5 kg/ha | 0 | 0 | 0 | 0 | 70 | 60 | 85 | 30 | 70 |
| dinoterbe 0.5 + I.P.U. 0.5 | 0 | 0 | 0 | 0 | 98 | 90 | 100 | 100 | 95 |

| Weeds: | II-Post-Emergence Test: | | | | | |
|---|---|---|---|---|---|---|
| | AV | RA | VU | MO | MT | RE |
| I.P.U. 0.5 kg/ha | 80 | 70 | 99 | 20 | 30 | 30 |
| Dinoterbe 0.5 kg/ha | 0 | 0 | 0 | 85 | 60 | 50 |
| I.P.U. 0.25 kg/ha + dinoterbe 0.25 kg/ha | 100 | 100 | 98 | 100 | 95 | 98 |

Similar results were obtained with mixtures respectively containing 0.24 + 0.16 kg/ha and 0.16 + 0.24 kg/ha of I.P.U + dinoterbe.

These results clearly reveal a degree of snyergy — insofar as the effect obtained with a given dose of the mixture — distinctly superior to that obtained with the same dose of each of the compounds used separately. In certain cases (rye-grass for example), the difference between 90 and 100% destruction may seem negligible. However, this is by no means the case because, in the event of heavy infestation by graminaceous weeds such as rye grasses, it is essential if weed control is to be economically worthwhile for destruction to be as close as possible to 100% because the density of weeds is such that even the survival of 10% is sufficient to cause considerable damage to the crop.

EXAMPLE 3

This Example corresponds to post-emergence tests carried out in the open on 30 square meter plots. One control is to set aside for each test.

The wheat on which the tests were carried out is of the Capitole variety. Treatment is carried out with wettable powders with an active material concentration of 60% on a cereal that has already emerged and is in the initial stages of tillering, the results being assessed after 45 days.

Under these conditions, it was found that, in doses of 4 kg/ha, the 50/50 mixture of I.P.U./monomethylamine salt of dinoterbe showed no signs whatever of phytotoxicity on the wheat, whereas the wheat was adversely affected by treatment with I.P.U. separately in the same dose. In addition, a high rate of destruction of the weeds present, namely wild spring oat, rye-grass, wild radish and may weed, was also observed.

In addition, under the same conditions, the complete destruction of rye-grass (*Lolium rigidum* and *Lolium multiflorum*) is obtained with the same 50:50 mixture in a dose of 3 kg/ha upwards, i.e. with 1.5 kg/ha of I.P.U. while the same effect is only obtained with I.P.U. separately in a dose of 1.8 kg/ha, dinoterbe being ineffectual against this weed in a dose of 1.5 kg/ha.

Similarly, the wild spring oat (*Avena fatua, Avena ludoviciana*) is completely destroyed by I.P.U. in a dose of 1.8 kg/ha in a 50/50 mixture with dinoterbe, while a dose of 2.4 kg/ha of I.P.U. separately is required to obtain the same result, dinoterbe being ineffectual against this weed when used on its own in a dose of 1.8 kg/ha.

Similar results were obtained with the same doses of 50/50 mixtures containing dinoterbe in phenolic form or in the form of its potassium or diethanolamine salt.

It is apparent from these tests that the addition of dinoterbe to I.P.U. virtually eliminates the phytotoxicity of I.P.U. on wheat. In addition, this mixture has a marked synergic effect on graminaceous weeds and an excellent action against dicotyledons.

Accordingly, the mixtures according to the invention are particularly suitable for safely, effectively and selectively controlling weeds growing among cereal crops, in particular wheat and barley, in post-emergence treatment.

They are characterized by a wide range of activity and by their rapid action which is sufficiently persistent to prevent the subsequent resprouting of weeds.

The respective percentage of the two compounds in the mixture can vary within wide limits. Interesting results have been obtained with mixtures containing from 0.5 to 3 parts of dinoterbe to 1 part of I.P.U.

Throughout the foregoing, reference has been made to dinoterbe or one of its derivatives. In the context of the invention, derivatives of dinoterbe are the various forms in which dinoterbe is normally used in practice, i.e. in phenolic form or in the form of its alkali salts, ammonium salts or aliphatic amine (monomethylamine, diethylamine, . . . ) salts or alkanolamine salts.

The doses in which the composition is used can vary within wide limits in dependence upon the activity of the composition used, the type of weed control to be obtained, the development stage of the crop and of the weeds and upon the type of soil and climatic conditions.

In general, active material doses of from 0.5 to 10 kg/ha are suitable.

For their practical application, the mixtures of active materials according to the invention are rarely used on their own. More often, they are part of formulations which generally comprise a support and/or a surfactant in addition to the active material according to the invention.

In the context of the invention, a support is an organic or mineral, natural or synthetic material with which the active material is associated to facilitate its application to the plant, to seeds or to the soil, or its transportation or handling. The support can be solid (clays, natural or synthetic silicates, resins, waxes, solid fertilizers . . . ) or fluid (water, alcohols, ketones, petroleum fractions, chlorinated hydrocarbons, liquified gases).

The surfactant can be an ionic or non-ionic emulsifier, dispersant or wetting agent. Reference is made by way of example to salts of polyacrylic acids, lignin sulphonic acid, condensates of ethylene oxide with fatty alcohols, fatty acids or fatty amines.

The compositions according to the invention can be prepared in the form of wettable powders, dusting powders, granulates, solutions, emulsifiable concentrates, emulsions, suspended concentrates.

The wettable powders are normally prepared in such a way that they contain from 20 to 95% by weight of active material. In addition to a solid support, they normally contain from 0 to 5% by weight of a wetting agent, from 3 to 10% by weight of one or more stabilizers and/or other additives, such as penetration agents, adhesives or anti-lumping agents, colorants, etc. The following is one example of the composition of a wettable powder:

| | |
|---|---|
| active material | 60% |
| calcium lignosulphate (deflocculant) | 5% |
| anionic wetting agent | 1% |
| anti-lumping silica | 5% |
| kaolin (filler) | 29% |

Aqueous dispersions and emulsions, for example compositions obtained by diluting a wettable powder or an emulsifiable concentrate according to the invention with water, are included in the general scope of the invention. These emulsions can be of the water-in-oil type or of the oil-in-water type and they can have a thick consistency resembling that of a "mayonnaise".

The compositions according to the invention can contain other ingredients, for example protective colloids, adhesives or thickeners, thixotropic agents, stabilizers or sequestrants and other active materials known to have pesticidal properties, in particular herbicides such as, in particular, mecoprop, dichlorprop, ioxynil, bromoxynil.

It will be obvious to those skilled in the art that various changes may be made without departing from the scope of the invention and the invention is not to be considered limited to what is described in the specification.

We claim:

1. An herbicidal composition for killing weeds growing among crops, consisting essentially of
   as active material an amount sufficient to kill said weeds without phytotoxicity to said crops, of a mixture of one part by weight of N-4-isopropylphenyl-N',N'-dimethylurea (I.P.U.) and 0.5 to 3 parts by weight of 2-4-dinitro-6-tert.-butyl-phenol (dinoterbe) or the alkali metal, ammonia and amine salts thereof,
   and an inert herbicidal carrier and a wetting agent.

2. Herbicidal composition as claimed in claim 1, wherein the metal salt is an alkali metal salt.

3. Herbicidal composition as claimed in claim 1, wherein the dinoterbe is used in the form of an amine salt.

4. Herbicidal composition as claimed in claim 1, wherein the dinoterbe is used in the form of alkanolamine salt.

5. Herbicidal composition as claimed in claim 3, wherein the dinoterbe is used in the form of monomethylamine salt.

6. A process for killing said weeds growing among said cereal crops, comprising applying to said crops or to the ground before emergence of said crops the composition of claim 1 in an amount sufficient to kill weeds without phytotoxicity to said crops.

7. A process as claimed in claim 6, wherein the herbicidal composition is applied to the crops in a post emergence treatment.

8. A process in accordance with claim 6, wherein said composition is applied at the rate of 0,5 to 10 kg/ha based on said active material mixture.

9. A process in accordance with claim 8 wherein said crop is wheat.

10. A process in accordance with claim 8 wherein said crop is barley.

11. A process in accordance with claim 8 wherein said crop is cotton.

12. A process in accordance with claim 8 wherein said crop is soya.

* * * * *